US00PP18170P2

(12) United States Plant Patent
Gossett

(10) Patent No.: US PP18,170 P2
(45) Date of Patent: Oct. 30, 2007

(54) ***PENSTEMON* PLANT NAMED 'CORAL CARPET'**

(50) Latin Name: ***Penstemon* spp.**
Varietal Denomination: Coral Carpet

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 5 days.

(21) Appl. No.: 11/452,715

(22) Filed: Jun. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct *Penstemon* plant characterized by deep pink flowers on numerous, very short, flowering stems, and with a compact habit.

1 Drawing Sheet

Botanical classification: *Penstemon* spp.
Variety denomination: 'Coral Carpet'.

BACKGROUND OF THE INVENTION

The present invention relates to a new and distinct cultivar of a suffrutescent perennial, *Penstemon* hybrid, and is given the cultivar name, 'Coral Carpet'. *Penstemon* are in the family Scrophulariaceae. This new cultivar which originated as an open pollinated seedling from *Penstemon* 'Pink Chablis' (U.S. Plant Pat. No. 13,422) progeny. Selections had been made yearly to improve the habit by making it more compact as well as to increase the bloom number, the number of inflorescences, and to reduce the height of the flower stalks.

SUMMARY OF THE INVENTION

This new cultivar is characterized by:

1) Deep pink flowers.
2) High flower number on a tight inflorescence.
3) Persistent basal foliage with a compact habit.
4) Numerous short flowering stalks.

This new cultivar has been reproduced only by asexual propagation (cuttings). Each of the progeny exhibits identical characteristics to the original plant. Asexual propagation by tip cuttings using standard propagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Penstemon* 'Coral Carpet' growing in the ground in full sun in the trial garden in Canby, Oreg.

DETAILED PLANT DESCRIPTION

The following is a detailed description of the new *Penstemon* hybrid based on observations of one-and-a-half-year-old specimens grown in the ground in full sun under typical outdoor conditions in Canby, Oreg. Canby is in Zone 8 on the USDA Hardiness map. Temperatures range from a high of 95 degrees F. in August to 32 degrees F. in January. Normal rainfall in Canby is 42.8 inches per year in the garden in Canby, Oreg. The color descriptions are all based on The Royal Horticultural Society Colour Chart.

Plant:
- *Type.*—Herbaceous perennial.
- *Form.*—Compact basal rosette.
- *Hardiness.*—USDA Zone 4 to 9.
- *Size.*—11 cm tall and 20 cm wide, not including bloom.
- *Habit.*—Suffrutescent, foliage doesn't die down in the winter.
- *Vigor.*—Good.
- *Roots.*—Fibrous, freely branching, white in color, White 155A. Roots develop slowly from stem cuttings.

Basal leaves:
- *Type.*—Simple.
- *Arrangement.*—Opposite on internodes growing to 11 mm long.
- *Shape.*—Oblanceolate to spatulate, fold up slightly.
- *Venation.*—Pinnate.
- *Margins.*—Entire.
- *Apex.*—Acute.
- *Base.*—Attenuate.
- *Blade size.*—Grows to 7 to 10 cm long and 14 to 17 mm wide.
- *Surface texture.*—Glabrous, shiny.
- *Petiole.*—Grows to 4 cm long, 3 mm wide, glabrous, Yellow Green 145B.
- *Leaf color.*—Deep green, Green 137A top and bottom, with prominent main vein on bottom, Yellow Green 144A.

Stem or cauline leaves:

*Type.*—Simple.

*Arrangement.*—Opposite on internodes growing to 3 cm long.

*Shape.*—Oblanceolate near the bottom and lanceolate near the top.

*Venation.*—Pinnate.

*Margins.*—Entire.

*Apex.*—Acuminate.

*Base.*—Sessile, obtuse.

*Blade size.*—Grows to 8.4 cm long and 2.4 cm wide.

*Surface texture.*—Glabrous, shiny.

*Leaf color.*—Deep green, Green 139A on top side and between Green 139A and Green 137A on bottom side, with prominent main vein on bottom, Yellow Green 145B.

Inflorescence:

*Type.*—Thyrse, virgate and weakly second.

*Number of thyrse.*—7.

*Number of flowers.*—30 to 56 per thyrse.

*Peduncle.*—Grows to 31 cm tall and 6 mm wide, Yellow Green 145A, glabrous.

*Pedicel.*—Grows to 1.5 cm long, glabrous, Yellow-Green 145A.

*Bloom period.*—June to July.

Flower bud:

*Size.*—2.8 cm long and 9 mm wide.

*Description.*—Closed tubular, bulging.

*Color.*—On upper half Red 51B and on lower half Red 51C with 7 to 8 lines of Greyed Purple 171B running from end to end.

Flower:

*Type.*—Perfect, zygomorphic.

*Shape.*—Tubular, bilabiate, with a 3 to 4 mm narrow tube for 7 mm, inflating to 11 mm for 9 mm, flaring into the lobes, the 10 mm wide and 12 mm deep top flare with two lobes shallowly cut 3 mm and overlapping, broadly ovate, entire, with acute tips; the bottom flare is strongly reflexed with three lobes divided to the base of the flare, lobes 9 mm deep and 7 mm wide, curling back, broadly oblong, entire, acute, entire.

*Size.*—3.2 cm long and 2.2 cm wide at flare.

*Color.*—Outside Red 55A overall with the underside slightly duller and with 7 to 8 stripes of Red Purple 59A, inside lobes are also Red 55A with bottom lobes each with one Red Purple 59A stripe down the center tapering almost to the tip, upper half of the inside tube is Red 55A lightening where inflated, bottom half of the tube inside is Red Purple 65A with the stripes Red Purple 59A.

*Calyx.*—5 lobes, glabrous, deeply cut, overlapping, ovate shaped lobes, margins irregularly serrate and scarious, acuminate tip, campanulate, 7 mm deep and 5 mm wide, Yellow Green 144A.

*Stamen.*—5 held within the corolla, one sterile without an anther, filaments 23 mm long, White 155A, anthers 2.5 mm long, pollen Yellow White 158B.

*Pistil.*—2.7 cm long, ovary 5 mm long and Yellow Green 144B, style 19 mm, Yellow White 158D.

*Fragrance.*—None.

*Lastingness.*—Each thyrse blooms for about 3 weeks on the plant.

Fruit:

*Type.*—Capsule.

*Fertility.*—Good.

*Size.*—1.2 cm deep and 4 mm wide.

*Color.*—Brown 200A to B.

Seed:

*Shape.*—Irregular.

*Size.*—2 mm long.

*Color.*—Brown 200A.

Disease and pest resistance: Excellent disease tolerance to root rot, a common problem for *Penstemon*. Leaf spot, rust, and powdery mildew may be a problem, but have not been observed on *Penstemon* 'Coral Carpet'.

Comparisons to similar *Penstemon:* Compared to *Penstemon* 'Pink Chablis' (U.S. Plant Pat. No. 13,422), this new cultivar has more compact overall with shorter and more numerous flowering stems.

I claim:

1. A new and distinct *Penstemon* plant substantially as shown and described.

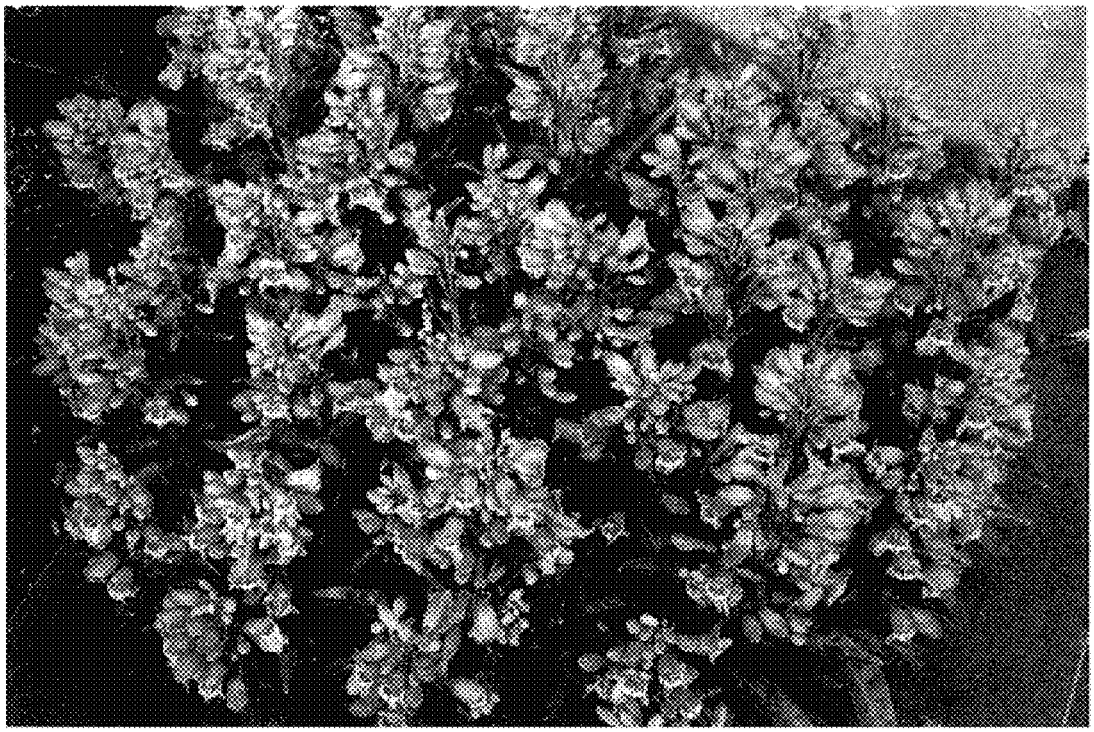

* * * * *